United States Patent
Hanson et al.

(10) Patent No.: US 11,060,989 B2
(45) Date of Patent: Jul. 13, 2021

(54) MICRONEEDLE-BASED ELECTRICAL IMPEDANCE SENSOR TO MONITOR PLANT WATER STATUS IN REAL TIME

(71) Applicants: National Technology & Engineering Solutions of Sandia, LLC, Albuquerque, NM (US); STC.UNM, Albuquerque, NM (US)

(72) Inventors: David T. Hanson, Albuquerque, NM (US); Philip Rocco Miller, Albuquerque, NM (US); Ronen Polsky, Albuquerque, NM (US); Patrick J. Hudson, Albuquerque, NM (US); Kaitlyn J. H. Read, Albuquerque, NM (US)

(73) Assignees: UNM Rainforest Innovations, Albuquerque, NM (US); National Technology & Engineering Solutions of Sandia, LLC, Albuquerque, NM (US)

(*) Notice: Subject to any disclaimer, the term of this patent is extended or adjusted under 35 U.S.C. 154(b) by 0 days.

(21) Appl. No.: 16/431,264

(22) Filed: Jun. 4, 2019

(65) Prior Publication Data
US 2019/0369039 A1 Dec. 5, 2019

Related U.S. Application Data

(60) Provisional application No. 62/680,682, filed on Jun. 5, 2018.

(51) Int. Cl.
*G01N 27/02* (2006.01)
*G01N 33/00* (2006.01)

(52) U.S. Cl.
CPC ....... *G01N 27/026* (2013.01); *G01N 33/0098* (2013.01)

(58) Field of Classification Search
CPC .................... G01N 27/026; G01N 33/0098
(Continued)

(56) References Cited

U.S. PATENT DOCUMENTS

| 9,737,247 B2 | 8/2017 | Wang et al. |
| 9,987,427 B1 | 6/2018 | Polsky et al. |

(Continued)

OTHER PUBLICATIONS

Jeon, E., Choi, S., Yeo, K.H., Park, K.S., Rathod, M.L. and Lee, J., 2017. Development of electrical conductivity measurement technology for key plant physiological information using microneedle sensor. Journal of Micromechanics and Microengineering, 27(8), p. 085009. (Year: 2017).*

(Continued)

*Primary Examiner* — Christopher P McAndrew
(74) *Attorney, Agent, or Firm* — R. Neil Sudol; Henry D. Coleman

(57) ABSTRACT

A sensor uses microneedle electrodes and multi-frequency electrical impedance spectroscopy to monitor plant water status in real time. The microneedle can be between 10 and 1000 microns in length, enabling precise placement in a variety of plant tissues. The impedance behavior can distinguish electrical properties and physiological functions of different plant tissue types. Therefore, impedance measurements can be used to monitor water stress to prevent irreversible damage to a plant and to enable improvement of plant biomass or fruit yield.

18 Claims, 6 Drawing Sheets

(58) Field of Classification Search
USPC .......................................................... 324/692
See application file for complete search history.

(56) References Cited

U.S. PATENT DOCUMENTS

| | | |
|---|---|---|
| 10,161,835 B1 | 12/2018 | Moorman et al. |
| 2017/0010296 A1* | 1/2017 | Shimokawa ....... G01N 33/0098 |
| 2018/0338713 A1 | 11/2018 | Polsky et al. |

OTHER PUBLICATIONS

Ren L, Xu S, Gao J, Lin Z, Chen Z, Liu B, Liang L, Jiang L. Fabrication of flexible microneedle array electrodes for wearable bio-signal recording. Sensors. Apr. 2018;18(4):1191. (Year: 2018).*

Kim, Y-C. et al. "Microneedles for Drug and Vaccine Delivery", Advanced Drug Delivery Reviews, 2012, pp. 1547-1568, vol. 64.

Miller, P.R. et al., "Microneedle-Based Sensors for Medical Diagnosis", Journal of Materials Chemistry B, 2016, pp. 1379-1383, vol. 4.

Miller, P.R. et al., "Microneedle-Based Transdermal Sensor for On-Chip Potentiometric Determination of K+", Advanced Healthcare Materials, 2014, pp. 876-881, vol. 3.

Grossi, M. et al., "Electrical Impedance Spectroscopy (EIS) for Biological Analysis and Food Characterization: A Review", Journal of Sensors and Sensor Systems, 2017, pp. 303-325, vol. 6.

Ando, Y. et al., "Electrical Impedance Analysis of Potato Tissues During Drying", Journal of Food Engineering, 2014, pp. 24-31, vol. 121.

Mizukami, Y. et al., "Moisture Content Measurement of Tea Leaves by Electrical Impedance and Capacitance", Biosystems Engineering, 2006, pp. 293-299, vol. 93.

Jamaludin, D. et al., "Impedance Analysis of Labisia Pumila Plant Water Status", Information Processing in Agriculture, 2015, pp. 161-168, vol. 2.

Hayden, R.I. et al., "Electrical Impedance Studies on Potato and Alfalfa Tissue", Journal of Experimental Botany, 1969, pp. 177-200, vol. 20.

Niikinmaa, E. et al., "Assimilate Transport in Phloem Sets Conditions for Leaf Gas Exchange", Plant, Cell & Environment, 2013, pp. 655-669, vol. 36.

Bartlett, M.K. et al., "The Determinants of Leaf Turgor Loss Point and Prediction of Drought Tolerance of Species and Biomes: A Global Meta-Analysis", Ecology Letters, 2012, pp. 393-405, vol. 15.

Kant, S. et al., "A Novel Crop Water Analysis System: Identification of Water Stress Tolerant Genotypes of Canola (*Brassica napus* L) Using Non-Invasive Magnetic Turgor Pressure Probes", Plant Breeding, 2014, pp. 602-608, vol. 133.

Miller, P. et al., "Electromolded Microneedles and Fabrication Methods Thereof", U.S. Appl. No. 16/286,081, filed Feb. 26, 2019.

* cited by examiner

MICRONEEDLE-BASED ELECTRICAL IMPEDANCE SENSOR TO MONITOR PLANT WATER STATUS IN REAL TIME

CROSS-REFERENCE TO RELATED APPLICATION

This application claims the benefit of U.S. Provisional Application No. 62/680,682, filed Jun. 5, 2018, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to methods to measure plant water status and, in particular, to a sensor that uses microneedle electrodes and multi-frequency electrical impedance spectroscopy to monitor plant water status in real time.

BACKGROUND OF THE INVENTION

Water is essential to maintain plant cell turgor and favor plant growth. Water stress can inhibit plant growth and production and can alter the biochemical properties of a plant. Plant water potential has long been recognized as a central regulator of plant physiology and growth. See J. S. Boyer, *Science* 218, 443 (1982). Current methods for monitoring water potential and metabolic fluctuations in plants largely involve destructive sampling of a harvested plant. Also, the harvested tissue has a limited time span for measurement, and is restricted to the tissue sampled (i.e., it cannot account for whole plant processes, or impacts of processes in other tissues/organs). See J. S. Boyer, *Plant Physiol.* 42, 133 (1967); and J. S. Boyer and E. B. Knipling, *Proc. Natl. Acad. Sci. USA* 54, 1044 (1965).

Therefore, a need remains for an in-situ direct sensor to measure plant water potential or turgor pressure easily and non-destructively to provide a real-time condition of the plant water status.

SUMMARY OF THE INVENTION

The present invention is directed to a sensor for monitoring plant water status, comprising at least two microneedle electrodes that can be inserted into a plant tissue and to which an alternating voltage or current can be applied therebetween to the plant tissue, and an electrical impedance analyzer to measure the impedance response of the plant tissue to the applied alternating voltage or current. Each microneedle electrode can comprise an array of one or more microneedles. Each microneedle can be between 10 and 1000 microns in length, enabling precise placement in a variety of plant tissues. The electrical impedance analyzer can measure an impedance response in a frequency range of 0.02 to 1000 kHz. The impedance behavior can distinguish electrical properties and physiological functions of different plant tissue types. In-situ measurements of the impedance can be used in a feedback loop that provides hydration to plants under stress. Therefore, impedance measurements can be used to monitor water stress to prevent irreversible damage to a plant and to enable improvement of plant biomass or fruit yield.

BRIEF DESCRIPTION OF THE DRAWINGS

The detailed description will refer to the following drawings, wherein like elements are referred to by like numbers.

DETAILED DESCRIPTION OF THE INVENTION

Figure 1:
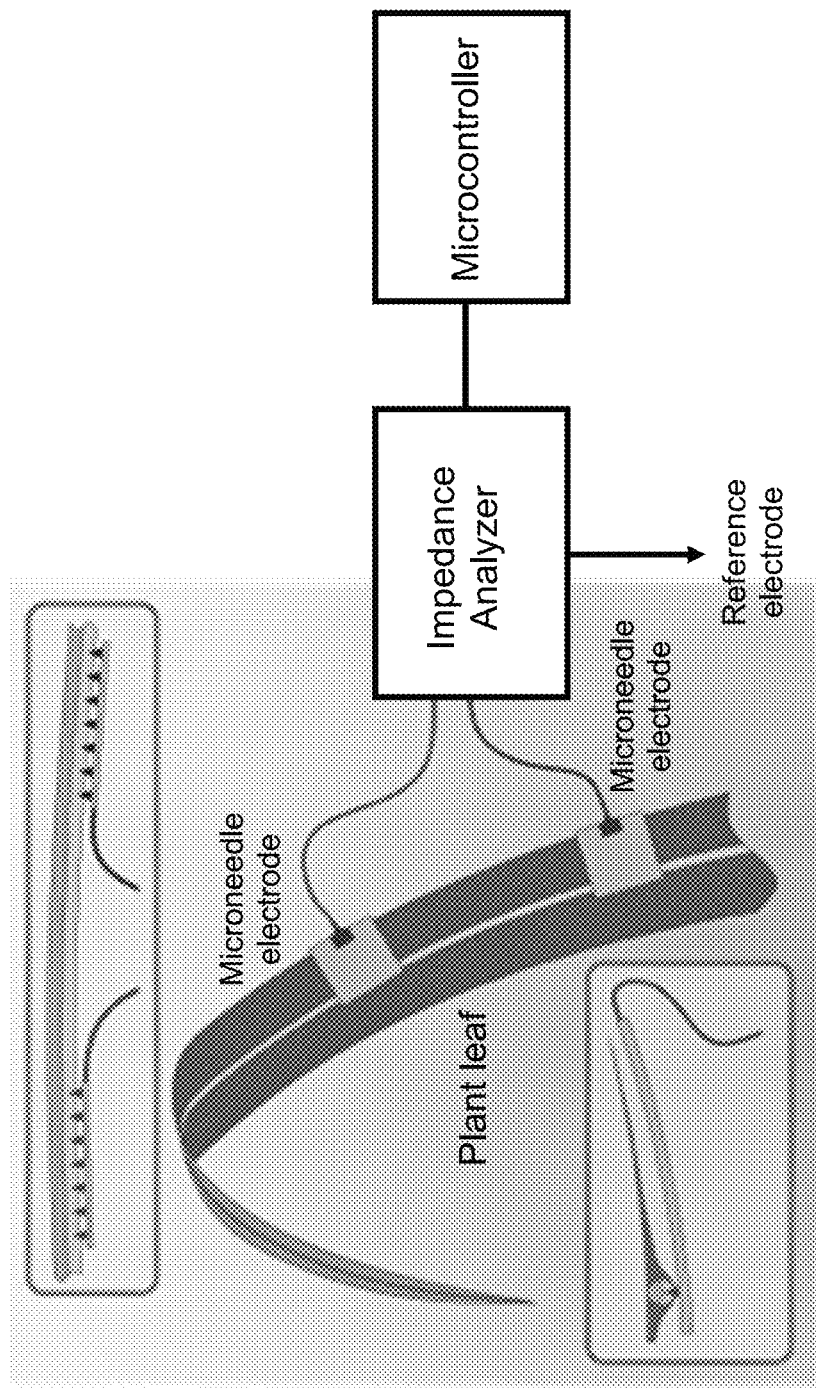
FIG. 1 is a schematic illustration of microneedle array placement in the midrib of a sorghum leaf. Microneedles can penetrate the highly capacitive epidermis on both the top and bottom of the sorghum leaf, targeting specific tissues without causing significant wound response.

The invention is directed to a sensor and method that use microneedles and multi-frequency electrical impedance spectroscopy (EIS) for the continuous monitoring of plant water potential and other data in the field and in real-time, without the need for a microscope or destructive sampling. As shown in FIG. 1, the sensor comprises at least two microneedle electrodes that can be inserted into the plant tissue, and an impedance analyzer that can measure the impedance response of the plant tissue to an alternating electrical signal (voltage or current) applied to a pair of microneedle electrodes in series. A plurality of such microneedle electrode pairs can be applied to the same plant or to multiple plants in dual or multi-terminal configurations. Each electrode can comprise an array of one of more microneedles. One of the electrode terminals can be placed in the soil surrounding the plant to measure impedance between a microneedle placed in the plant and the soil-based electrode for monitoring root function and growth. A microcontroller can be used to control the various impedance sensors and send or store data from the impedance analyzer continuously while consuming low power.

Microneedles are microscale devices similar in shape and functional to hypodermic needles that have been used for both transdermal drug delivery and wearable sensors due to their minimally invasive nature. See Y. C. Kim et al., *Adv. Drug Deliv. Rev.* 64(14), 1547 (2012); U.S. Pat. No. 10,161, 835 to Moorman et al., issued Dec. 25, 2018, Pub. No. U.S. 2018-0338713 to Polsky et al., published Jan. 29, 2018; U.S. Pat. No. 9,987,427 to Polsky et al., issued Jun. 5, 2018; and U.S. Pat. No. 9,737,247 to Wang et al., issued Aug. 22, 2017, which are incorporated herein by reference. Their size 000 microns in length) restricts interaction with deeper layers of human skin, making them amenable to long-term use without discomfort. See P. R. Miller et al., *J. Mater. Chem. B*

4(8), 1379 (2016). The microneedles of the present invention can be from ~10 to ~1000 microns in length to allow for similar precision placement in a plant tissue. Tissue cross-sections confirm precision placement of microneedles in targeted tissues in leaves, enabling tissue-specific monitoring in plant organs, including stems, roots, and fruits, across all varieties of plants. For example, the microneedles can be inserted directly into specific tissues of Sorghum bicolor leaves and can target specific tissues in other crops. For example, the microneedles can be sized to penetrate the strongly insulating epidermal layer, permitting the low-frequency EIS necessary for apoplastic/symplastic distinction. For plant monitoring, the microneedles can be solid or hollow, and can include micro-probes or wires. Each microneedle electrode can comprise an array of microneedles, wherein the microneedles are spaced 1-2 mm apart in the array. The array can be less than 1 cm$^2$ and can be attached to a plant with clothes pins, tape, or glue. Therefore, the microneedles can be used as nondestructive sensors to provide real-time monitoring of metabolic events in plants to improve plant function and productivity.

Figure 2:
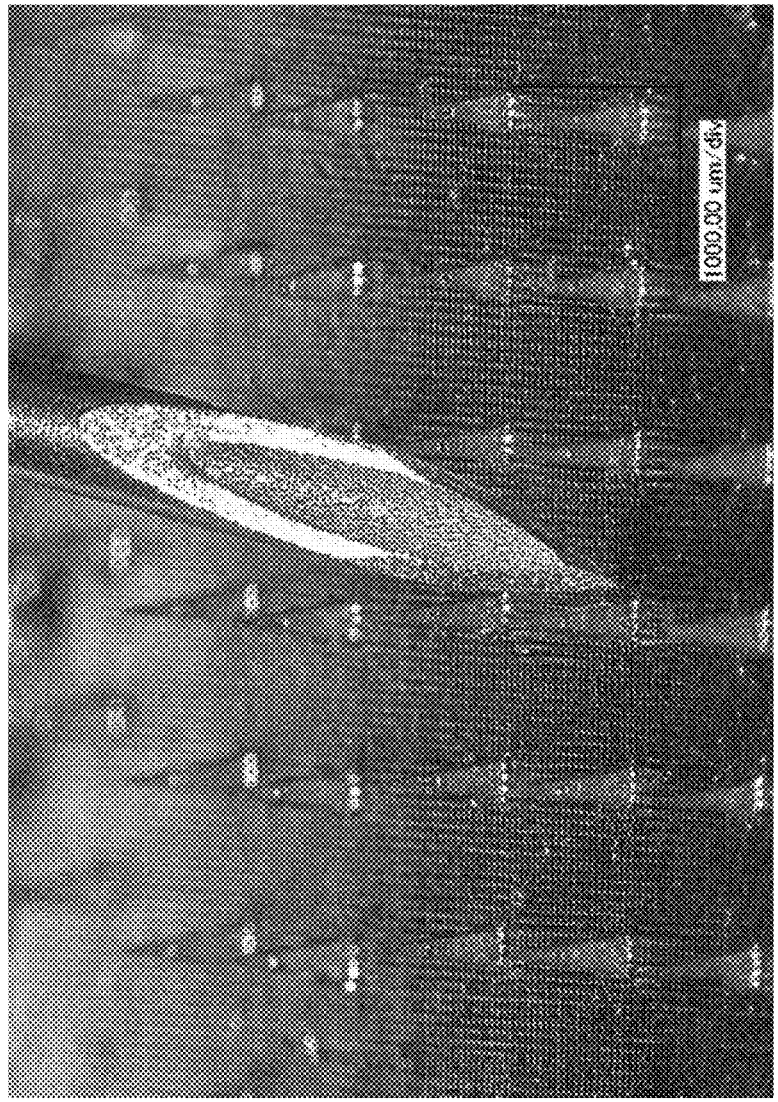
FIG. 2 is a photograph of a single 22-gauge syringe shown relative to an array of hollow metal microneedles.
Figure 3:
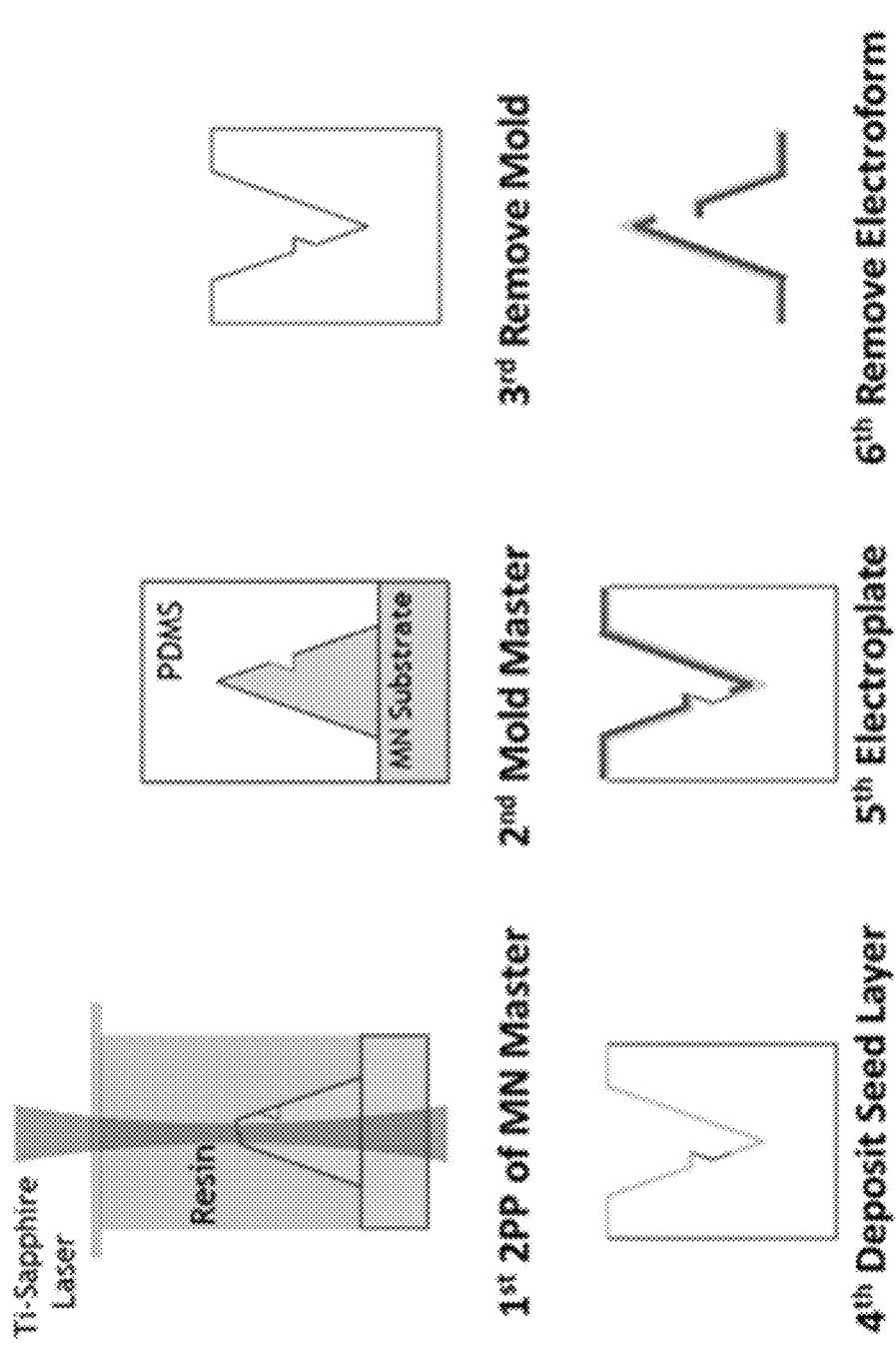
FIG. 3 is a schematic illustration of an electromolding process for the fabrication of hollow metallic microneedle arrays.

Microneedles can be fabricated using an electromolding technique, which offers a unique method of making hollow microneedles that are inherently strong. While solid microneedles are much easier to fabricate due to their simpler design, they can be more challenging to incorporate into sensing systems due to the lack of a hollow bore. Therefore, the present invention can use hollow microneedles, as shown in FIG. 2. A microneedle master structure can be made with a two-photon polymerization system utilizing laser direct write, which creates 3D structures with sub-micron resolution based on user defined CAD files. See P. R. Miller et al., *Adv. Healthc. Mater.* 3(6), 876 (2014). This method provides flexibility not found in many other manufacturing tools but is limited in throughput. Because of this issue, an electromolding method can be used to fabricate the microneedle arrays, as shown in FIG. 3. See U.S. application Ser. No. 16/286,081 to Miller, filed Feb. 26, 2019, which is incorporated herein by reference. With this method, a microneedle master is molded with polydimethylsiloxane (PDMS) from a microneedle substrate. The microneedle substrate can then be removed to provide a PDMS template. The template can then be coated with a conducting seed layer onto which the microneedle material can be electroplated. The electroformed needle can then be removed from the PDMS mold. This additional processing post-master fabrication method allows for numerous electroforms to be created simultaneously due to the industrially proven scalability of electroplating. Dozens of molds can be made from a single master, thus enhancing the production value of a rapid prototyping system. Since the microneedle and substrate can be made from strong metal multi-layer foils, the substrate offers a flexible, conformal backing that has been tested to withstand various deformations, similar to those expected from wearable use, without permanent deformation. Arrays of microneedles can be manufactured on a flexible backing that can make application to each plant tissue as easy as sticking on a band-aid, since having an array of needles attached makes the likelihood of hitting targeted cells high.

The sensor of the present invention can be used as an early warning surveillance system to provide real-time information on plant water status using EIS. See M. Grossi and B. Ricco, *J. Sens. Sens. Syst.* 6, 303 (2017); Y. Ando et al., *J. Food. Eng.* 121, 24 (2014); Y. Mizukaml et al., *Biosyst. Eng.* 93(3), 293 (2006); and D. Jamaludin et al., *Inf. Process. Agric.* 2, 161 (2015), which are incorporated herein by reference. EIS is a non-destructive method that measures the dielectric properties of a medium as a function of frequency and can be used for characterizing materials and biological systems by studying frequency dependent impedance signals. By passing a low voltage (or current) across a range of frequencies between two microneedle arrays, EIS can measure changes in the passive electrical properties of tissues and a user can gather information about the overall health of a plant. For example, a small-amplitude sinusoidal voltage (or current) can be applied to the plant tissue and the output current (or voltage) can be measured to derive the complex impedance over a suitable frequency range using a multi-frequency impedance analyzer. Typically, the data is represented with a Nyquist plot, in which the imaginary component (reactance) of the complex impedance is plotted against the real component (resistance) for each frequency.

The data can be interpreted using an equivalent circuit model of the plant tissue. See R. Hayden et al., *J. Exp. Bot.* 20, 177 (1969). Accordingly, the physiological status of the plant tissue can theoretically be quantified by monitoring the changes in the electrical parameters of the equivalent circuit. Plant tissues comprise cells suspended in extracellular fluids. The cells themselves are comprised of intracellular fluids, a cell membrane, and a cell wall. At low frequency (~0.02-10 kHz), the electrical current flows mainly through the extracellular fluid, due to the high electrical capacity of the plant cell membranes at low frequencies. In plants, the extracellular fluids act as electrolytes and have a relatively high impedance. The electrical impedance of the plant material decreases with increasing frequency due to the reduced capacitance of the plant cell membrane, enabling flow through the low-resistance intracellular fluid at high frequency (~10-1000 kHz). Therefore, the impedance declines markedly from the low to high frequency range of the spectrum. See Y. Ando et al., *J. Food. Eng.* 121, 24 (2014).

Since moisture will affect the electrical properties of the plant tissue, EIS can be used to monitor the water potential of a plant. In particular, changes in water potential and ion concentration can be determined by measuring the change in resistance across multiple frequencies. Typically, the real component of frequency is lower for well-hydrated plants. Conversely, plants with lower water potential can have higher impedance values, as stressed plants conduct electricity poorly. Measuring the ion concentrations in the plant can provide an indicator of the overall water potential and heath of the plant. For example, the microneedle data can enable in-field assessment of limitations on phloem transport due to reduced function of the plants hydraulic system (xylem) and the associated photosynthetic feedback. See E. Nikinmaa et al., *Plant Cell Environ.* 36, 655 (2013). EIS can also measure the integrity of cell membranes, because the phospholipid bilayer acts as a capacitor. Due to the capacitive nature of cell membranes, low and high frequencies can be used to distinguish apoplastic (outside the cell) and symplastic (inside the cell) ion concentrations, respectively. Therefore, water potential and cell membrane integrity can indicate plant stress.

A variety of microcontrollers, which function as small computers, can be used to control the various sensors and send or store data from the impedance analyzer continuously while consuming low power. According to a specific embodiment, a commercially available microcontroller, such as the Arduino mini controller, can be used to control the various sensors. This controller can be a low power system requiring only 23 uA for operation and is about the size of a postage stamp. An autonomous system can communicate with sensors, send or store their data, and be scaled to investigate large plant populations. The controller can further be used in a feedback loop to analyze the impedance response from the impedance analyzer and provide water to a plant when they reach desired water potentials.

Figure 4:
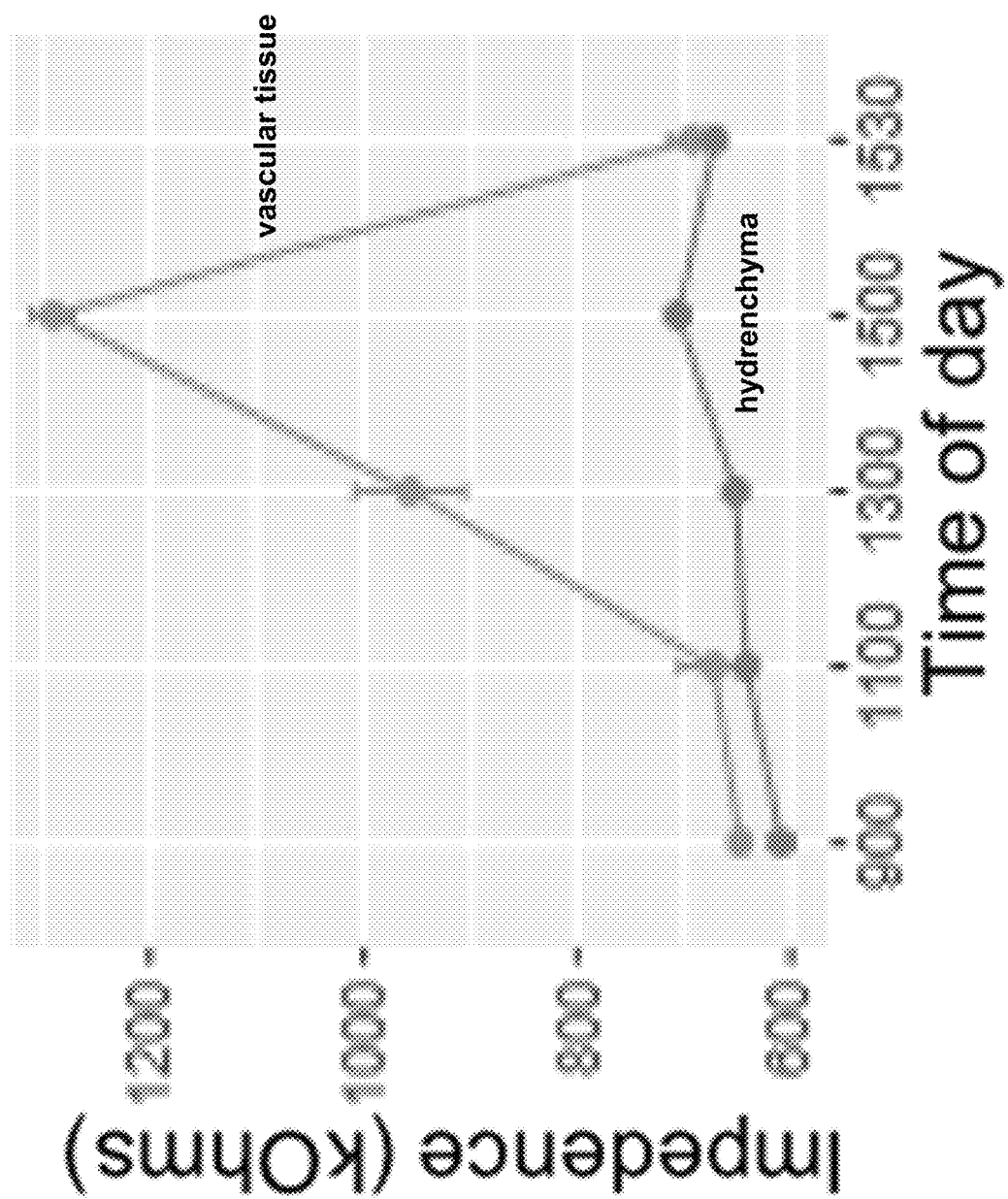
FIG. 4 is a graph of tissue specific impedance responses to mild drought stress in vascular tissue and in hydrenchyma.

The sensors can monitor the changing activity in two tissues on the same leaf and their individual responses to watering. Placement of the microneedle probe on one side or the other of a sorghum leaf produces a different electrical impedance due to the different physiological processes on either side of the leaf (i.e., water storage versus water transport). The impedance changes, or lack thereof, reflect the extracellular processes and tissue dynamics associated with the amount of water present. In FIG. 4, watering was ceased at 0900, causing dehydration of the plant, and resumed at 1500, causing the plant to rehydrate. Ion concentrations decreased proportionally with drought onset (0900-1500 h) in vascular tissue but remained constant in hydrenchyma. When water was supplied at 1500 h, ion concentration increased more rapidly in vascular tissue than hydrenchyma.

The microneedle sensors can be used for monitoring the water status of plants. For example, the microneedles can provide a minimally invasive mechanism to monitor water potential and turgor pressure. Turgidity is the hydrostatic pressure exerted on cell walls by osmotic flow of water through the semipermeable cell membrane. The inward diffusion of water causes an increase in turgor pressure, and vice versa. Turgor pressure provides structural rigidity, and this pressure can be an indicator of overall plant health due to water related stress. See M. K. Bartlett et al., *Ecol. Lett.* 15(5) 393 (2012). In particular, turgor pressure is high when the cell membrane pushes against the cell wall (i.e., turgid) and low when the cell membrane is flaccid, as evidenced by plant wilt. Turgor pressure also plays a key role in plant growth, due to the irreversible expansion of the extensible cell wall due to the force of turgor pressure.

The stochastic nature of climate change can produce environments where crops are exposed to continually challenging and unpredictable conditions leading to fluctuating water resources, which can threaten plant growth and productivity. Portable devices for monitoring turgor pressure can provide valuable tools for assessing water requirements of new cultivars to help farmers converse water and save money by optimizing water usage depending on environmental conditions. The plant research community has begun to develop minimally invasive tools for assessing plant turgor pressure for these very reasons. The microneedles of the present invention can provide a minimally invasive avenue to monitor turgor pressure in a broad variety of crop plants. A particular advantage of the microneedles is their compatibility with small leaves, typical of crops in the arid southwest landscape, which may not be physically suited to "wear" a larger device. See S. Kant met al., *Plant Breeding* 133(5), 602 (2014).

Water potential measures the tendency of water to move from one region of a plant to another, for example, by osmosis, gravity, or capillary action. Addition of solutes, such as dissolved salts, typically lowers the potential, whereas an increase in pressure or elevation will raise the water potential. With no restriction to flow, water will move from a region of high water potential to a region of lower water potential (pure water has a reference potential of zero). Therefore, water potential can indicate the demand for water within the plant, the resistance to water movement within the plant, and water loss by transpiration to dissipate heat and cool the leaves. See P. Kramer, Water Relations of Plants, Elsevier Science (2012).

Figure 5:
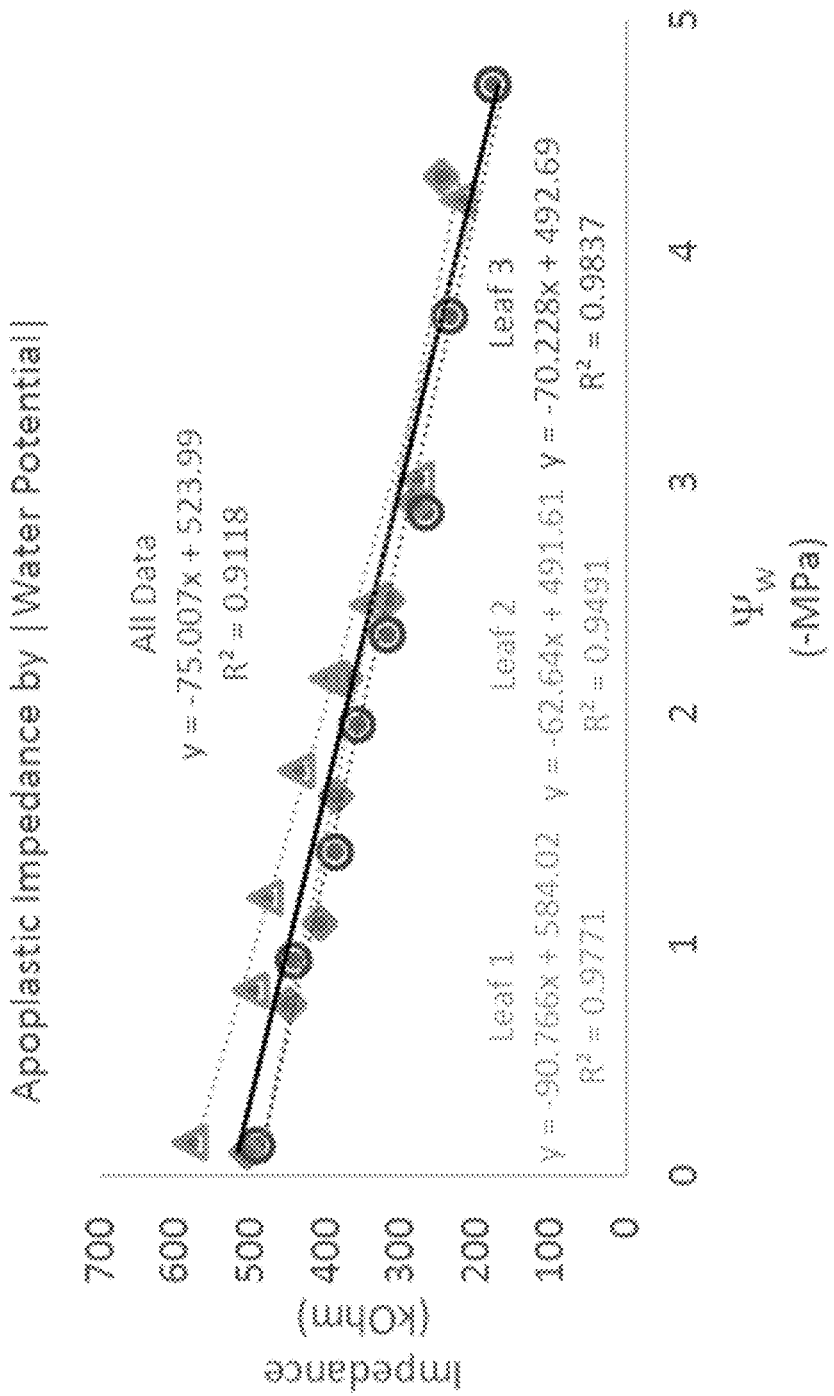
FIG. 5 is a graph of the correlation of impedance with bulk leaf water potential, both within and across sampled leaves of *Populus deltoides*, indicating the utility of electrical impedance spectroscopy for monitoring plant water status.

Correlations can be developed between direct measurements of plant water potential and impedance at various frequencies. FIG. 5 shows plots of impedance versus bulk leaf water potential, as determined by pressure bomb measurements, both within and across sampled leaves of *Populus deltoids* at a frequency of 0.1 kHz. The graph indicates a good correlation between water potential and low frequency impedance. As expected, a leaf with low water potential has a high impedance value, as it conducts electricity poorly.

Figure 6:
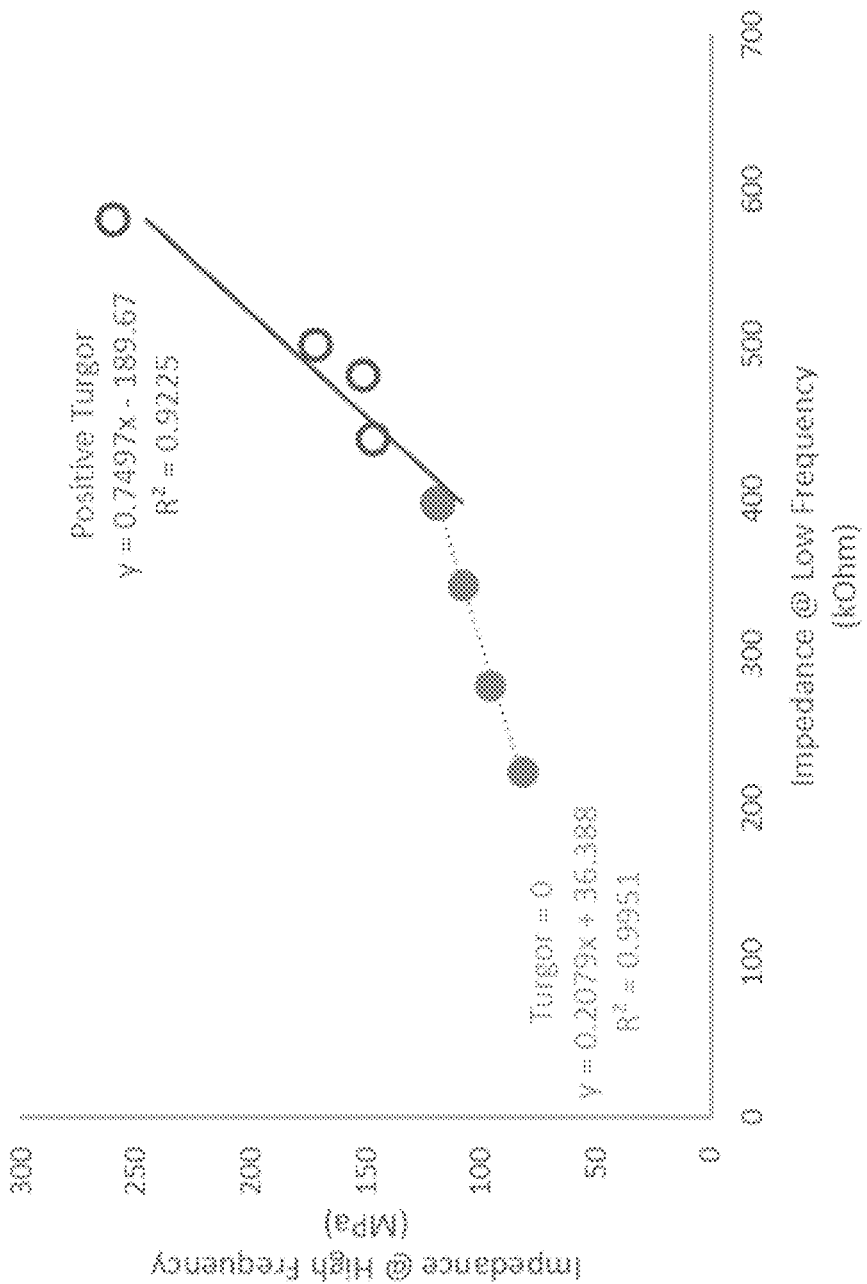
FIG. 6 is a bivariate plot of impedance ratios. The intersect at the value of impedance at low frequency translates to the water potential of turgor loss.

In addition, ratios of impedance at various frequencies can be determined, as shown in FIG. 6. When high and low frequency impedance results are plotted against each other, two linear regions are seen with their intersection being the turgor loss point (TLP). Concurrently, the TLP was determined via pressure bomb measurements. The TLP is the pressure at which the hydrostatic pressure in the cell sap is equal to atmospheric pressure, such that no net force is exerted on the cell wall and water begins to flow out of the leaf. The EIS and pressure bomb measurements of TLP are in good agreement, as shown in Table 1. The TLP indicates the capacity of a plant to maintain cell turgor pressure during dehydration, which has been proven to be predictive of the plant response to drought.

TABLE 1

Comparison of water potential at turgor loss (Turgor Loss Point, TLP) as calculated from pressure/volume curves (PV) and electrical impedance spectroscopy (EIS) measurements made on dehydrating leaves of *Populus deltoides*.

| Sample | $TLP_{PV}$ (MPa) | $TLP_{EIS}$ (MPa) | % Error |
| --- | --- | --- | --- |
| Populus_01 | −1.75 | −1.83 | 4.92% |
| Populus_02 | −1.69 | −1.70 | 0.36 |
| Populus_03 | −1.95 | −1.84 | 5.62 |
| Populus_04 | −1.29 | −1.25 | 3.25 |
| Populus_05 | −1.62 | −1.49 | 7.99 |
| Average | −1.63 | −1.60 | 2.27 |

Student's t-test: p = 0.89

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

We claim:

1. A sensor for monitoring plant water potential, comprising:
    at least two microneedle electrodes that can be inserted into a plant tissue and to which an alternating voltage or current can be applied therebetween to the plant tissue, and an electrical impedance analyzer to measure the impedance response of the plant tissue to the applied alternating voltage or current, wherein each microneedle is between 10 and 1000 microns in length.

2. The sensor of claim 1, wherein the electrical impedance analyzer can measure an impedance response in a frequency range of 0.02 to 1000 kHz.

3. The sensor of claim 1, wherein each microneedle electrode comprises an array of two or more microneedles.

4. The sensor of claim 1, further comprising a reference electrode.

5. The sensor of claim 1, further comprising a controller to analyze the impedance response and provide water to the plant when the sensor detects desired water potentials.

6. The sensor of claim 1, wherein the microneedles are configured for insertion into the tissue so that the microneedles are spaced from each other by at leas one millimeter.

7. A method for monitoring plant water potential, comprising:
    providing at least two microneedle electrodes configured for insertion into plant tissue;
    attaching said at least two microneedle electrodes to a plant so that said at least two microneedle electrodes are in electrical contact with a pre-selected type of plant tissue;
    applying, to the pre-selected type of plant tissue, an alternating voltage or current of a first frequency via said at least two microneedle electrodes;
    subsequently applying, to the pre-selected type of plant tissue, an alternating voltage or current of a second frequency via said at least two microneedle electrodes, said first frequency being in a first range and said second frequency being in a second range, all frequencies in said first range being different in frequency than all frequencies in said second range;
    analyzing electrical impedance of the pre-selected type of plant tissue between the at least two microneedle electrodes to determine a first impedance response of the pre-selected type of plant tissue to the applied alternating voltage or current at said first frequency;
    analyzing electrical impedance of the pre-selected type of plant tissue between the at least two microneedle electrodes to determine a second impedance response of the pre-selected type of plant tissue to the applied alternating voltage or current at said second frequency; and
    determining, from said first impedance response and said second impedance response, a correlation between measurements of plant water potential and impedance at the first frequency and at the second frequency.

8. The method of claim 7 wherein the determining of the correlation includes forming a ratio of the first impedance response and the second impedance response.

9. The method of claim 7 wherein the attaching of said at least two microneedle electrodes to said plant includes attaching said at least two microneedle electrodes to a pre-selected side of a leaf.

10. The method of claim 9 wherein said pre-selected side of said plant leaf is an underside of said plant leaf.

11. The method of claim 7 wherein said pre-selected type of tissue is vascular tissue.

12. The method of claim 7 wherein one of said first frequency and said second frequency is in a range between about 0.02 and 10 kHz and the other of said first frequency and said second frequency is in a range between about 10 and 1000 kHz.

13. A device for monitoring plant water potential, comprising:
    a sensor including at least two microneedle electrodes that can be inserted into plant tissue to monitor plant tissue response to applied electrical voltage, said sensor including means for applying, to the plant tissue via said at least two microelectrodes, an alternating voltage or current of a first frequency and subsequently an alternating voltage or current of a second frequency, said first frequency being in a first range and said second frequency being in a second range, all frequencies in said first range being different in frequency than all frequencies in said second range; and
    an electrical impedance analyzer operatively connected to said sensor to measure the impedance response of the plant tissue to the applied alternating voltage or current; and
    a controller operatively connected to the sensor to control the sensor and operatively connected to the electrical impedance analyzer to analyze the electrical impedance of the pre-selected type of plant tissue between the at least two microneedle electrodes to determine a first impedance response of the pre-selected type of plant tissue to the applied alternating voltage or current at said first frequency and to further analyze electrical impedance of the pre-selected type of plant tissue between the at least two microneedle electrodes to determine a second impedance response of the pre-selected type of plant tissue to the applied alternating voltage or current at said second frequency, to thereby enable determination of a correlation between measurements of plant water potential and impedance at the first frequency and at the second frequency.

14. The device of claim 13, wherein said controller is configure to provide water to the plant when the sensor detects desired water potentials.

15. The device of claim 13 wherein one of said first frequency and said second frequency is in a range between about 0.02 and 10 kHz and the other of said first frequency and said second frequency is in a range between about 10 and 1000 kHz.

16. The device of claim 13, wherein each microneedle electrode comprises an array of two or more microneedles.

17. The device of claim 13, further comprising a reference electrode.

18. The device of claim 13, wherein the controller is configured to send or store data from the impedance analyzer continuously.

* * * * *